United States Patent [19]

Gratzek et al.

[11] 4,309,416

[45] Jan. 5, 1982

[54] VACCINES FROM TAXONOMICALLY SIMILAR ORGANISMS

[75] Inventors: John B. Gratzek, Athens, Ga.; Beverly A. Goven, Bellevue, Wash.; Donald L. Dawe, High Shoals, Ga.

[73] Assignee: Research Corporation, New York, N.Y.

[21] Appl. No.: 77,269

[22] Filed: Sep. 20, 1979

[51] Int. Cl.³ .......................................... A61K 39/002
[52] U.S. Cl. ..................................................... 424/88
[58] Field of Search ................................... 424/88–93, 424/128

[56] References Cited

U.S. PATENT DOCUMENTS

| | | | |
|---|---|---|---|
| 994,660 | 6/1911 | Schmidt | 424/88 |
| 2,202,435 | 5/1940 | Shoetensack | 424/89 |
| 3,119,741 | 1/1964 | Freedman et al. | 424/88 |
| 3,285,817 | 11/1966 | Slater | 424/89 |
| 3,326,767 | 6/1967 | Holper et al. | 424/89 |
| 3,429,965 | 2/1969 | Gelenczei et al. | 424/89 |
| 3,450,815 | 6/1969 | Fishbein | 424/88 |
| 3,465,077 | 9/1969 | Baker | 424/89 |
| 3,518,347 | 6/1970 | Pavilanis et al. | 424/89 |
| 3,541,206 | 11/1970 | Hall | 424/89 |
| 3,548,054 | 12/1970 | Bowen et al. | 424/89 |
| 3,577,525 | 5/1971 | Baker | 424/89 |
| 3,642,574 | 2/1972 | Okazaki et al. | 424/89 |
| 3,657,415 | 4/1972 | Jennings et al. | 424/88 |
| 3,674,864 | 7/1972 | Angelucci | 424/89 |
| 3,849,551 | 11/1974 | D'Antonio | 424/88 |
| 3,876,764 | 4/1975 | Straub | 424/89 |
| 3,927,209 | 12/1975 | Straub | 424/89 |
| 4,009,259 | 2/1977 | Ament et al. | 424/89 |
| 4,039,656 | 8/1977 | Straub | 424/89 |
| 4,049,794 | 9/1977 | Straub | 424/89 |
| 4,053,582 | 10/1977 | Stickl | 424/89 |
| 4,201,763 | 5/1980 | Monthony et al. | 424/8 |
| 4,208,479 | 6/1980 | Zuk et al. | 424/8 X |
| 4,220,450 | 9/1980 | Maggio | 424/8 X |

FOREIGN PATENT DOCUMENTS

| | | | |
|---|---|---|---|
| 2238433 | 3/1975 | France | 424/88 |
| 2274314 | 2/1976 | France | 424/89 |
| 2302103 | 10/1976 | France | 424/88 |
| 7969 | 4/1913 | United Kingdom | 424/88 |
| 1059095 | 2/1967 | United Kingdom | 424/89 |
| 1277134 | 6/1972 | United Kingdom | 424/88 |

OTHER PUBLICATIONS

Hlond, Stefan "Experiments in Vitro Culture of *Ichthyophthirius multifiliis*" FAO Fisheries Reports V. 44(S):365–368 (1968).

Beckert "Observations on the Biology of *Ichthyophthirius multifiliis*... and Some Immunological Responses of Channel Catfish, *Ictalurus punctatus* to This Parasite" Dissertation Abstr. Int. 36B, 11,5461 (1976).

Chem. Abstracts 9th Coll. Index 76-85, 1972–1976 "*Tetrahymena pyriformis*" pp. 15516GS–15518GS.

Becker et al. "Some Host Response of White Catfish to *Ichthyophthirius multifiliis* Foquet" Proc. 18th Ann. Conf. S.E. Assoc. Game & Fish Comm. (1964).

Areerat"The Immune Response of Channel Catfish, *Ictalurus punctatus* (Rafinesque) to *Ichthyophthirius multifiliis*" Master's Thesis, Auburn, Univ. Ala. (1974).

Primary Examiner—Shep K. Rose
Attorney, Agent, or Firm—Oblon, Fisher, Spivak, McClelland & Maier

[57] ABSTRACT

A vaccine for protection against an infectious organism which cannot be readily cultured in vitro comprising an antigen derived from a taxonomically similar organism which is readily cultured in vitro. The method of preparation and the method of use are also disclosed.

6 Claims, No Drawings

VACCINES FROM TAXONOMICALLY SIMILAR ORGANISMS

BACKGROUND OF THE INVENTION

1. Field of the Invention

This invention is directed to vaccines and there preparation from organisms taxonomically similar to the infective organism.

2. Description of the Prior Art

Immunotherapy with respect to infectious organisms has generally followed the theory of using either the organism itself or some intermediate state in its development as the basis for production of an immunizing vaccine. In this regard, the art is replete with examples of the effectiveness of this approach. For instance, immunization of chickens against cecal coccidiosis by establishing a controlled subclinical infection (U.S. Pat. No. 3,147,185); non-living vaccine produced by incubation of third-stage nematode larvae into the histotrophic stages (U.S. Pat. No. 3,395,218 and German Auslegesschrift No. 1,160,139); canine hookworm vaccine comprising a physiologically acceptable aqueous vehicle containing attenuated premigratory live hookworm larvae (U.S. Pat. No. 3,657,415); an Ascaris suum vaccine comprising sonicated third-stage larvae, sonicated second stage larvae, larvae hatching fluid and second-stage larval culture fluid (U.S. Pat. No. 3,676,547); an antigen preparation for immunoprecipitin diagnostic testing for Chagas' disease, caused by *Trypanosoma cruzi*, comprising purified, water-soluble antigen obtained from tissue culture of *Trypanosoma cruzi* to essentially only the trypomastigote and amastigote growth stages (U.S. Pat. No. 3,911,097); vaccine comprising a live, but attenuated, metazoan endoparasite which is pathogenic to domestic animals and is a nematode, trematode or cestode in the form of eggs or a premigratory or a migratory immature form (British Pat. No. 819,830 and Canadian Pat. No. 602,465); a vaccine comprising a metazoan or protozoan endoparasite, which elicits an immune response in the host, attenuated with a sub-lethal dose of ultraviolet radiation (British Pat. No. 902,760) and a vaccine comprising an antigen of Schistosoma mansoni separated from a development stage of the parasite (German Offenlegungsschrift No. 2,742,835). Additionally, a vaccine for canine hookworm has been produced which comprises a physiologically acceptable aqueous vehicle containing premigratory live hookworm larvae of a hookworm species which is specific to cats (British Pat. No. 1,277,134).

However, a need continues to exist for the preparation of vaccines against infectious organisms, which are either difficult or impossible to culture, in vitro, on a commercially practical scale. Exemplary of infectious organisms which cannot be readily cultured, in vitro, on a commercial scale are *Ichthyophthirius multifiliis* and *Cryptocaryon irritans*.

*Ichthyophthirius multifilius* and *Cryptocaryon irritans* are some of the most damaging parasites of warm water and salt water fish, respectively, and some of the most difficult to control. Experimental immunization of catfish with *Ichthyophthirius multifiliis* has been reported (Becker et al, "Some Host Response of White Catfish to *Ichthyophthirius multifiliis* Fouquet", Proc. 18th Ann. Conf. S.E. Assoc. Game and Fish Comm., 1964). Additional studies have shown that channel catfish injected intraperitoneally with vaccine prepared from the ground trophozoites, with and without Freund's adjuvant, survived challenge whereas control suffered 100% mortality after seven days (Areerat, S., "The Immune Response of Channel Catfish, *Ictalurus punctatus* (Rafinesque) to *Ichthyophthirius multifiliis*", Masters Thesis, Auburn University, Auburn, Ala. (1974)).

No known method exists for growing the protozoans *Ichthyophthirius multifiliis* and *Cryptocaryon irritans*, in vitro. Both *Ichthyophthirius multifiliis* and *Cryptocaryon irritans* are obligate parasites, the infective tomites must penetrate a host within 24-48 hours or perish. For this reason, maintenance of the parasites requires continual passage to susceptible hosts. Therefor, the accumulation of sufficient antigen to immunize large numbers of fish is very time-consuming and impractical.

*Ichthyophthirius multifiliis* and *Cryptocaryon irritans* are devastating parasites because they have a high morbidity and mortality. The diseases affect not only food fish, including trout, salmon, catfish, carp, eel, tuna, and bonita, but also ornamental fish. At present, chemical treatments are the only practical way of controlling the disease. These treatments including malachite green, formalin, methylene blue, potassium permanganate and others are not approved for use on food fish by the USDA.

Furthermore, malachite green, the most effective treatment, may soon be banned from use on any fish. Because of the limitations of chemotherapy, immunotherapy may be the only successful and practical approach to controlling these diseases.

A need therefore, continues to exist for a vaccine to immunize fish from the ravages of *Ichthyophthirius multifiliis* and *Cryptocaryon irritans* which can be readily produced on a scale suitable for aquacultural operations.

SUMMARY OF THE INVENTION

Accordingly, one object of the invention is to provide an effective vaccine for immunization against infectious organisms which are difficult or impossible to culture, in vitro.

A further object of the invention is to provide a vaccine for immunization againt a pathogen derived from a taxonomically similar organism.

A further object of the invention is to provide a commercially feasible method of producing a vaccine for immunization against infectious organisms on a scale suitable for commercial operations.

A further object of the invention is to provide an effective vaccine for the immunization of fish against *Ichthyophthirius multifiliis* and *Cryptocaryon irritans*.

A further object of the invention is to provide a commercially feasible method of producing a vaccine for fish on a scale suitable for aquacultural operations.

Briefly, these objects and other objects of the invention as hereinafter will become more readily apparent can be obtained by providing a vaccine for protection against infection by an organism which cannot be readily cultured in vitro which comprises an antigen derived from a taxonomically similar organism which may be readily cultured, in vitro.

DETAILED DESCRIPTION OF THE PREFERRED EMBODIMENTS

Taxonomy is the orderly classification of organisms into appropriate categories on the basis of relationships among them, e.g., species, genus, family, order or class. Applicants have discovered that by careful analysis of these relationships, it is possible to select suitable pairs of organisms wherein antigenic cross-reactivity may be used to develop a vaccine for one of the organisms based on the other of the organisms.

Taxonomic similarity is now found to be an ideal basis for selection of organisms suitable for use in the preparation of a vaccine. Taxonomic similarity is determined through fluorescent staining techniques. In particular, an animal, such as a rabbit, is innoculated with the pathogen; blood serum is collected from the rabbit, i.e. antibodies are collected; the pathogen is then contacted with the blood serum, allowing interaction of the antigen and antibody; the so-contacted pathogen is then stained with a fluorescent stain which is selective for the site of antibody-antigen interaction, e.g. staining with FITC labelled anti-rabbit IgG; the gross morphology of the so-stained pathogen is then examined to determine the sites of greatest intensity of staining, e.g. cilia, flagella, mouth and the like; based on the localization of high intensity staining, an organism, suitable for use as a source of vaccine, is selected which has identical physical features to those producing the highest intensity of staining in the pathogen. Desirably, additional factors such as body shape, pathogenicity for the host and ease of culturation may be used in selection of the organism suitable for preparation of a vaccine. For example, the minimum taxonomic relationship appropriate as an indicia of antigenic cross-reactivity for the parasites *Ichthyophthirius multifiliis* and *Cryptocaryon irritans* would be that of a ciliate. In particular, for the protozoans *Ichthyophtirius multifiliis* and *Cryptocaryon irritans,* a protozoan having the characteristics of being easily cultivable, having cilia and being pathogenic for fish would be highly suitable. Such ciliate organisms would induce immunity, to *Ichthyophthirius mulltifiliis* and *Cryptocaryon irritans,* when used in the preparation of vaccine.

This approach allows the selection of a particular organism, to be cultured for the production of antigen, wherein the organism selected may be selected on the basis of commercial viability- i.e., ease of production and cost, rather than solely on the criteria that it is the disease source. More importantly, this approach allows the use of large-scale commercial culturing techniques for the production of antigens for infectious organisms which organisms are not generally amenable to such culturing techniques. Typically, the organisms which are not susceptible to culturation, in vitro, are those which cannot be sustained in presently available culture media, i.e. organisms which only propagate in a living host. Exemplary of such organisms are *Ichthyophtirius multifiliis* and *Cryptocaryon irritans.*

Ichthyophthiriasis, and its saltwater counterpart, produced by *Cryptocaryon irritans,* are epizootic diseases which claim high mortalities in aquaculture. *Ichthyophthirius multifiliis* and *Cryptocaryon irritans* are holotrichous ciliates which are ectoparasitic on the gill and hypodermis of fish. The infective stage or tomite penetrates the epithelium where it encysts and develops into the parasitic stage. Macroscopically, these encysted forms produce the condition popularly known as "white spot disease" or "ick".

These parasites are known to cause severe epizootics in the culture of food fish, as well as ornamental fish. They are a major problem in high density ponds because the common chemical treatments are ineffective in removing the encysted stage. The encysted stage, after several maturation processes, divides into thousands of infective tomites, perpetuating the infection. Additionally, the common chemical treatments are also toxic to certain species and may be particularly dangerous in the treatment of young fish. The trend towards high density food fish production has increased the importance of this disease.

The infective tomites of *Ichthyophthirius multifiliis* and *Cryptocaryòn irritans* morphologically resemble the holotrichous ciliate, *Tetrahymena pyriformis. Tetrahymena pyriformis,* a carnivorous protozoan, is considered an opportunistic parasite of fish, rarely producing a primary disease. The close taxonomic association between these ciliates allows the use of antigenic cross-reactivity similar to the antigenic relatedness of canine distemper and measles virus.

The adult form of *Tetrahymena pyriformis* and the tomites of *Ichthyophthirius multifiliis* and *Cryptocaryon irritans* are similar in that they are all covered by cilia and that they are all pear (pyriform) shaped. The differences are that tomites of *Ichthyophthirius multifiliis* and *Cryptocaryon irritans* actively pentrate the skin of fish to form adult forms called trophozoites. *Tetrahymena pyriformis* does not induce classical "Ick" disease. Taxonomically, therefore, the three organisms are ciliates but belong to different genera.

The development of Tetrahymena pyriformis as an "heterotropic vaccine" for *Ichthyophthirius multifiliis* or *Cryptocaryon irritans* is efficacious for several reasons:

(1) *Tetrahymena pyriformis,* a free living protozoan, is easily maintained in vitro using simple medium. Tetrahymena pyriformis is easily cultivated in the laboratory using a medium of water and almost any nitrogenous compound. Suitably, the medium is as simple as water with a protein source and a carbohydrate source. A medium of sterile water plus almost any other source of organic material found in a wide diversity ordinary bacteriological culture mediums is suitable, such as, sterile water plus 2–5% of sterile calf serum. A particularly preferred medium is Elliot Medium #2 (*Biology of Tetrahymena;* Elliot, A. M.; Bowden, Hutchinson and Ross, Inc.; Stroudsburg, Pa. (1973)).

| FORMULA FOR ELLIOT MEDIUM #2 | |
|---|---|
| Sodium Acetate $3H_2O$ | 1.0g |
| $KH_2PO_4$ | 1.0g |
| Proteose peptone | 20.0g |
| Liver Extract "L" | 1.0g |
| Glucose* | 5.0g |
| Water | q.s. to 1000 ml |

*glucose - filter, sterilize and add to medium after autoclaving

Cultivation takes place at a temperature in the range of about 0° to 35° C., preferably at about 26° C.

(2) *Tetrahymena pyriformis is naturally found in the same environment as Ichthyophthirius multifiliis.*

(3) *Tetrahymena pyriformis, a relatively benign organism, can be used to protect against the pathogens Ichthyophthirius multifiliis* and *Cryptocaryon irritans* based on the fact that selected antigens, i.e. cilia and mouth parts, are identical between these organisms.

A vaccine may be prepared by using the whole protozoan to produce a vaccine, i.e. disintegrating the whole protozoan to produce a vaccine. However, the cilia are readily removable and such use of the cilia is efficacious. The disintegration of the whole protozoan may be accomplished by techniques well-known in the art, e.g. grinding with a mortar and pestile, sonication, chemical treatment and enzyme treatment. The important point is that ciliary antigens protect the fish by producing an immunity.

Preferentially, the vaccine comprises cilia stripped from Tetrahymena pyriformis according to the method of Rosenbaum (Rosenbaum, J. L. "Cilia Regeneration in Tetrahymena and its Inhibition by Colchicine", J. Cell Bio 40, p. 415 (1969)).

The antigenic material, i.e. the ciliary protein, may be separated from the whole cilia to more effectively concentrate the antigen.

Concentration may be achieved by methods known in the art, e.g., pervaporation, centrifugation and concentration by utilization of carbowax. preferentially, the protein is concentrated with methyl cellulose and dialyzed against phosphate buffered saline (PBS) at 4° C. The protein concentration can then be assayed by the method of Lowry (Lowry et al., "Protein Measurement with the Follin Phenol Reagent", J. Biol. Chem., 193, p. 265 (1951)).

The vaccine additionally may comprise acceptable diluents, excipients or medicinal agents. Any substance which would not destroy or interfere with the antigenic material, i.e. ciliary protein, may be incorporated in the vaccine. Such substances include buffers, stabilizers, antibiotics, bacterial vaccines and nutritional supplements. Any acceptable diluent may be used, preferably, the vaccine is prepared in aqueous form. The vaccine may also include one or more adjuvants.

The vaccine may be adminstered by intraperitoneal injection, in capsule form, incorporated into food, and in the case of fish, by immersion of fish, or by spraying fish suspended in a net.

For mass aquacultural operations, immersion or spraying are preferred techniques. Such techniques are well known for the administration of bacterial vaccines. Preferably, the vaccine is mixed with one or more bacterial vaccines when administered by immersion or spraying. Additionally, when adminstration is by the spray technique, it is preferable to include Bentonite in the spray formulation so as to enhance penetration and uptake of the vaccine.

The dosage of antigen may be determined by the method of Hall (Hall et al, "Characterization Of A Teleost Immunoglobulin: The Immune Macroglobulin From Channel Catfish", *Comm. Biochem. Physiol.* 46, pp. 187–197 (1973)).

In the case of a vaccine for Ichthyophthirius multifiliis or Cryptocaryon irritans derived from Tetrahymena pyriformis, the dosage rate is generally at least 2.5 micrograms of ciliary protein per 20 grams of fish. Preferably, the dosage rate is about 5 micrograms of ciliary protein per 20 grams of fish.

The vaccine may be prepared as a concentrate and then diluted for use as needed. Lyophilization is a suitable method for the preparation of a concentrate. Alternatively, the vaccine may be stored at room temperature for short periods of time or may be kept frozen when long storage times are contemplated.

Vaccines prepared by the techniques set forth herein may suitable be applied to both lower and higher forms of life, e.g., fish, domestic animals and man. Typical examples include trout, salmon, catfish, carp, eel, tuna, bonito, dogs, cats, sheep cattle, horse and human.

Having essentially described this invention, a further understanding can be obtained by reference to certain specific examples which are provided herein for purposes of illustration only and are not intended to be limiting upon the scope of the invention.

EXAMPLE 1

Cultivation of *T. pyriformis*

An axenic culture of *T. pyriformis* was obtained (Midwest Culture Service, Terre Haute, Ind.). Cultures were maintained in an enriched medium at pH 7.2 to 7.4. (Elliot Medium #2). All cultures were incubated aerobically at 26° C. At approximately three-week intervals fresh media was inoculated with 10% (v/v) of the old culture.

EXAMPLE 2

Cultivation of *I. multifiliis*

*I. multifiliis* was maintained by serial passage in channel catfish (*Ictalurus punctatus*), which were kept in a 38 liter (10 gallon) glass aquarium equipped with an undergravel filter. *I. multifiliis* was maintained in this manner for eight months.

EXAMPLE 3

Maintenance of Channel Catfish

"Young of the Year" channel catfish, *Ictalurus punctatus* Rafinesque, were obtained from a commercial farm (J. Sims, Winder, Ga). Fish were kept in a 950 liter (250 gallon) flow-through stainless steel tank and were fed flake food (Kordon Corp., Hayward, Calif.) supplemented with ground chicken liver on alternating days. For experimentation, fish were removed from the holding tank and allotted into 38 liter (10 gallon) glass aquaria equipped with undergravel filters. Aeration was provided by a central air supply attached to the air lift system of the gravel filter. Fish were sustained on the same diet schedule. Ammonia measured as $NH_3$-N and nitrate measured as $NO_2$-N were monitored throughout the experiments by standard test kits (LaMotte, Chestertown, Md.). Water was changed as necessary to avoid the accumulation of toxic products.

EXAMPLE 4

Preparation of *T. pyriformis* for Antigen

Ten- to fourteen-day old cultures were used for antigen preparation. Organisms from 20 ml of culture were concentrated by centrifugation at 500 xG for 10 minutes (IEC Universal Model UV, International Equipment Co., Needham Hts., Mass.). The sediment was washed twice with phosphate buffered saline (PBS), resuspended in 2.5 ml of PBS and immediately used in the deciliation procedure. Deciliation was effected by a cold osmotic shock process followed by shearing through an 18 g needle (Rosenbaum et al.). Deciliated cells were nonmobile. Ten ml of PBS was added to the tubes containing the deciliated cells, and the cells were concentrated by centrifugation for 10 minutes at 500 xG. The supernatant containing free cilia was decanted, placed in dialysis tubing, and concentrated with carboxymethyl cellulose. The concentrated cilia then were dialyzed overnight in PBS (pH 7.2) at 4° C. The deciliated cells were resuspended in PBS and stored at 4° C. for later use as whole cell antigen. The protein concentrations of whole cell and ciliary antigen were determined (Lowry et al.).

EXAMPLE 5

Preparation of *I. multifiliis* for Antigen

Encysted trophozoites were removed from infected channel catfish by gentle scraping. The cysts are incubated at room temperature (20°C.) in sterile distilled water containing 10 ml/l chloromycetin sodium succinate (Parke-Davis, Detroit, Mich.) and 0.025 mg/l fungizone (GIBCO, Grand Island, N.Y.). After 18-24 hours, free swimming tomites were decanted, concentrated and deciliated in the same manner as described for *T. pyriformis* in Example 4.

EXAMPLE 6

In Vitro Testing

Sera from fish and rabbits immunized with cilia and whole *T. pyriformis* cross-reacted with tomites of *I. multifiliis*. This antigenic relationship was demonstrated using three in vitro tests:

A. Immobilization Test

In immobilization studies, live *T. pyriformis* exposed to rabbit antitetrahymena serum agglutinated at low dilutions and were immobilized at high dilutions. Tomites of *I. multifiliis* exposed to the same serum were immobilized within two hours. Titers in this heterologous test were 1:32 and 1:128. In contrast, immobilization titers in the homologous system were 1:1024.

B. Indirect Fluorescent Antibody Test

The treatment of both *T. pyriformis* and *I. multifiliis* with either rabbit anti-tetrahymena or rabbit anti-ichthyophthirius sera lead to similar patterns of fluorescence when the organisms were stained with FITC labelled anti-rabbit IgG. With both organisms, the hightest staining was seen in the surface structures.

C. Passive Hemagglutination Test

The passive hemagglutination test was used to provide a more sensitive indication of the cross-reactivity between *I. multifiliis* and *T. pyriformis*. In this test heterologous titers of 1:1024 were obtained (sheet erythrocytes tanned with Tetrahymena and rabbit anti-ichthyophthirius). These tests also showed cross-reactivity and indicate that an antigenic relationship exists between these two organisms, localized on ciliary antigens.

EXAMPLE 7

In Vivo Testing

Twenty-five catfish, each weighing approximately 20 g, were allotted into 38 liter glass aquaria. Antigen was prepared as described in Example 4 and Example 5. The dosage of antigen per body weight of fish was determined according to Hall et al. (*Com. Biochem. Physiol.* 46:187-197 (1973)). Fish were immunized by intraperitoneal injection of antigen diluted to working concentration with phosphate buffered saline (PBS). Each antigen dose was run in duplicate. Twenty-five nonimmunized fish served as controls. The experimental groups were: (1) Tetrahymena cilia 5 µg; (2) deciliated Tetrahymena 10 µg; (3) Ichthyophthirius cilia 2.5 µg; and (4) deciliated Ichthyophthirius 2.5 µg. Higher concentrations of tetrahymenid antigen were used because of the cross-reacting relation. Fifteen days after the initial immunization, booster injections were administered. Fish immunized with the tetrahymenid antigens received the same dose, while fish immunized with Ichthyophthirius cilia received 3.5 µg and deciliated Ichthyophthirius 4.5 µg, respectively. Fifteen days following the booster injections, an "Ich" infected contact fish was placed into each tank. The fish were observed for clinical signs of infection and mortality. The results are set forth in the following table:

TABLE I

Mortality of Channel Catfish Immunized with Ciliary and Whole Antigens of *T. pyriformis* and *I. multifiliis*, and Challenged With *I. multifiliis*,* Two Weeks Following Secondary Immunization

| Antigen | Primary Dose | Secondary Dose | Total # Fish | % Mortality |
|---|---|---|---|---|
| *T. pyriformis* cilia | 5.0 µg | 5.0 g | 137 | 11.6 |
| Whole (deciliated) | 10.0 µg | 10.0 g | 89 | 100.0 |
| *I. multifiliis* cilia | 3.5 µg | 3.5 g | 120 | 42.5 |
| Whole (deciliated) | 2.5 µg | 4.5 g | 76 | 77.6 |
| Nonimmunized | | | 25 | 100.0 |

*Fish with clinical Ichthyophthiriasis were placed in each tank to expose experimental fish to disease.

Primary immunization of catfish with 5 µg of T. pyriformis ciliary antigen, followed by a secondary immunization with 5 µg of antigen two weeks later, conferred an excellent degree of protection against challenge with *I. multifiliis* when the fish were challenged two weeks after booster. Only 11.6% of the fish in these groups developed clinical disease. Fish immunized with 10 µg of deciliated whole cells, followed two weeks later with the same dose, were not protected against infection and died when exposed to the disease. Homologous immunization with deciliated whole *I. multifiliis* cells (2.5 µg, 4.5 µg) resulted in 77.6% mortality following challenge with *I. multifiliis*. Mortality was 42.5% in fish immunized with homologous ciliary antigen (3.5 µg, 3.5 µg). Mortality was 100% in the control groups.

Having now fully described this invention, it will be apparent to one of ordinary skill in the art that many changes and modifications can be made thereto without departing from the spirit or scope of the invention set forth herein.

What is claimed as new and intended to be covered by letters patent is:

1. A veterinary vaccine for immunizing fish against infection by *Ichthyophthirius multifiliis* and *Cryptocaryon irritans* comprising an effective amount of ciliary protein derived from *Tetrahymena pyriformis* cilia and an inert diluent.

2. A method of immunizing fish against infection by *Ichthyophthirius multifiliis* and *Cryptocaryon irritans* which comprises administering to the fish the vaccine of claim 1.

3. The method according to claim 2, wherein the vaccine is administered orally.

4. The method according to claim 2, wherein the vaccine is administered by immersion.

5. The method according to claim 2, wherein the vaccine is administered by spraying.

6. The method according to claim 2, wherein the vaccine is administered by injection.

* * * * *